United States Patent
Hoock et al.

(10) Patent No.: US 8,222,282 B2
(45) Date of Patent: Jul. 17, 2012

(54) SULFONATE SALTS OF 2-AMINO-3-CARBETHOXYAMINO-6-(4-FLUORO-BENZYLAMINO)-PYRIDINE

(75) Inventors: Christoph Martin Hoock, Dresden (DE); Asal Qadan, Dresden (DE)

(73) Assignee: Teva Pharmaceuticals USA, Inc., North Wales, PA (US)

( * ) Notice: Subject to any disclaimer, the term of this patent is extended or adjusted under 35 U.S.C. 154(b) by 282 days.

(21) Appl. No.: 12/481,097

(22) Filed: Jun. 9, 2009

(65) Prior Publication Data

US 2009/0318506 A1 Dec. 24, 2009

(30) Foreign Application Priority Data

Jun. 9, 2008 (EP) .................................... 08010471

(51) Int. Cl.
*C07D 213/04* (2006.01)
*A61K 31/44* (2006.01)

(52) U.S. Cl. ....................................... 514/352; 546/308
(58) Field of Classification Search ........................ None
See application file for complete search history.

(56) References Cited

U.S. PATENT DOCUMENTS

2006/0252804 A1* 11/2006 Pieroth et al. ............. 514/352

FOREIGN PATENT DOCUMENTS

| DE | 17 95 858 | 4/1978 |
|----|-----------|--------|
| DE | 31 33 519 | 6/1982 |
| DE | 33 37 593 | 5/1984 |
| DE | 39 15 184 | 11/1989 |
| EP | 0 160 865 | 11/1985 |
| EP | 0 615 754 | 7/2002 |
| EP | 0 977 736 | 9/2003 |
| EP | 1 795 186 | 6/2007 |
| EP | 08010471.4 | * 6/2008 |
| WO | WO 2004/112754 | 12/2004 |

OTHER PUBLICATIONS

Hoock et al, PCT/US2009/046726 filed Jun. 9, 2009.*
Kuhnert-Brandst, M. et al "Contribution to Polymorphism of Drugs 7th Communication: Famotidine, Flupirtine Maleate, GYKI-51189, Paxamate, Propentofylline, and Triclabendazole" Scientia Pharmaceutica, vol. 58, p. 55-67, (1990).
Caira, M.R. "Crystalline Polymorphism of Organic Compounds", Topics in Current Chemistry, vol. 198, p. 163-208, (1998).
Landgraf, K.F. et al. "Polymorphism and desolvation of flupirtine maleate", European Journal of Pharmaceutics and Biopharmaceutics, vol. 46, p. 329-337, (1998).

* cited by examiner

*Primary Examiner* — Zinna Northington Davis
(74) *Attorney, Agent, or Firm* — Arent Fox LLP

(57) ABSTRACT

Flupirtine acid addition salts having the following formula (2),

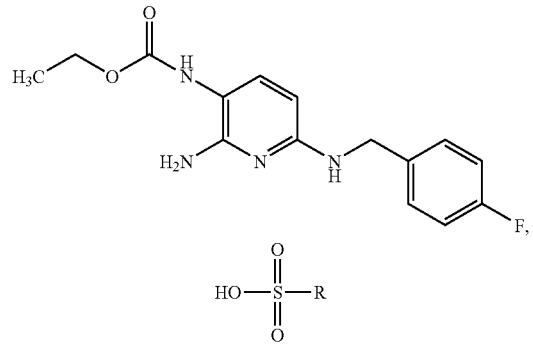

(2)

wherein R represents a substituted or unsubstituted $C_1$-$C_{12}$-alkyl or a substituted or unsubstituted $C_6$-$C_{10}$-aryl group, have been prepared.

5 Claims, 7 Drawing Sheets

Figure 1. A photomicrograph of flupirtine mesilate.
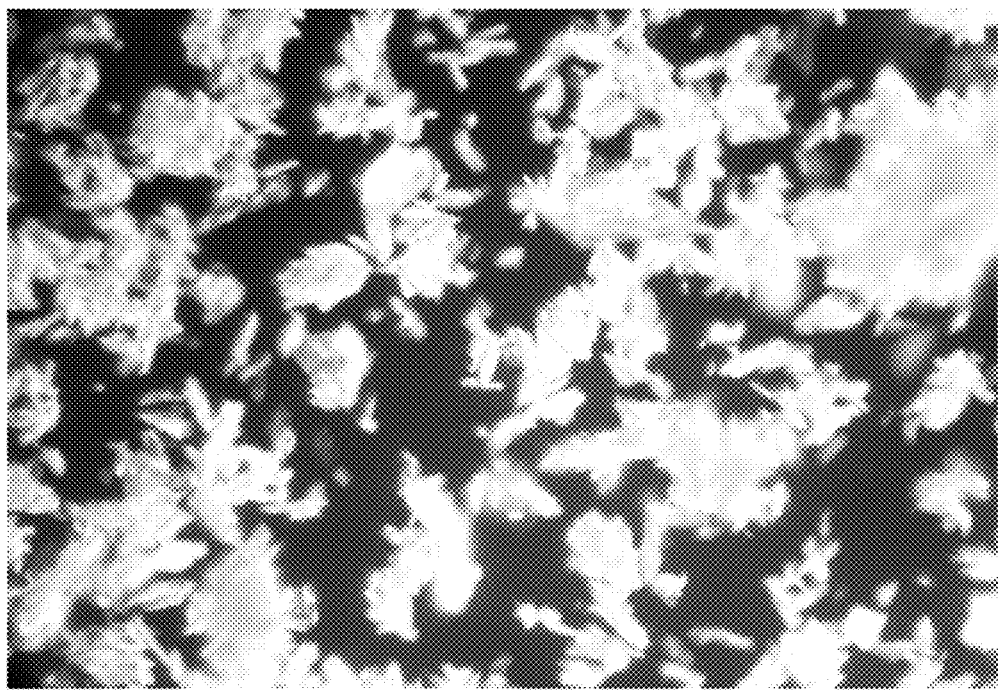

Figure 2. A photomicrograph of flupirtine maleate
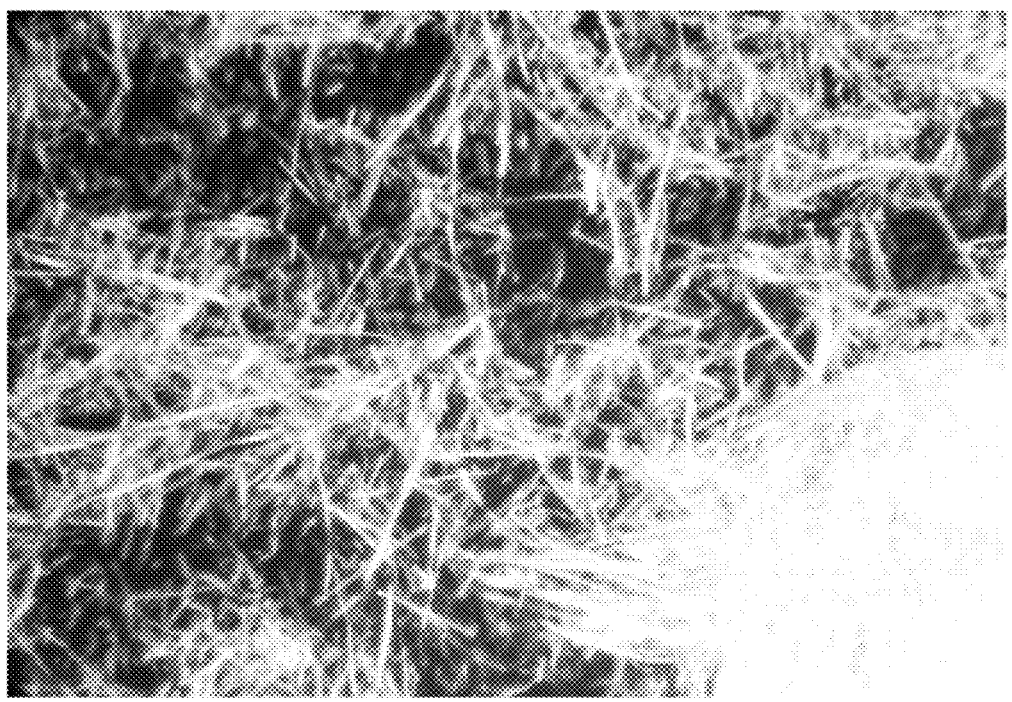

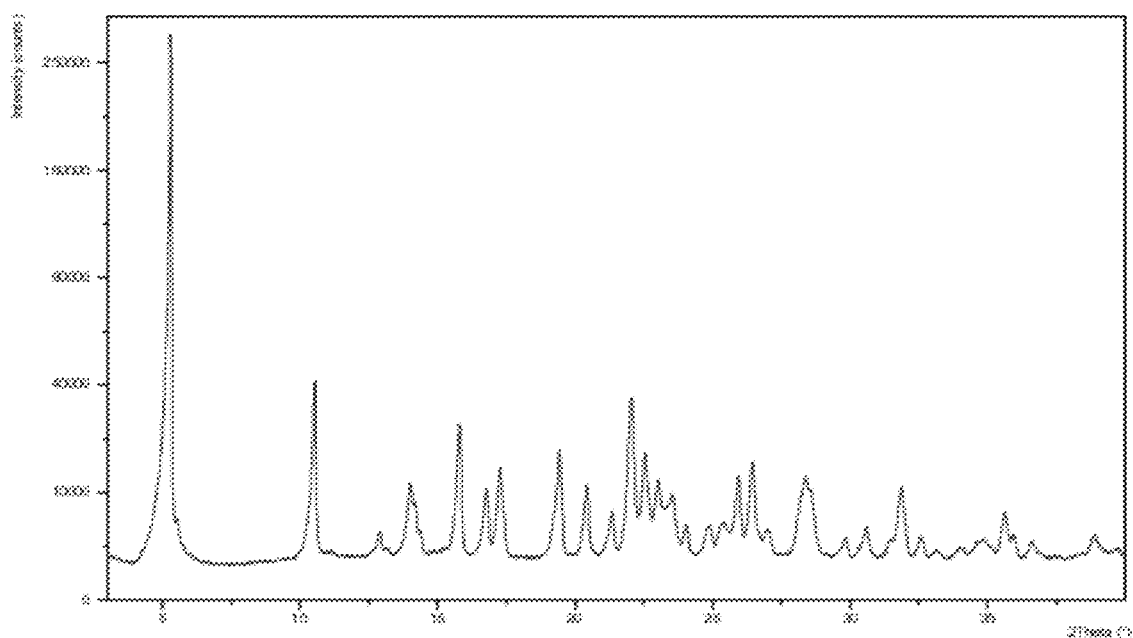
Figure 3. X-ray powder diffraction pattern of flupirtine mesilate

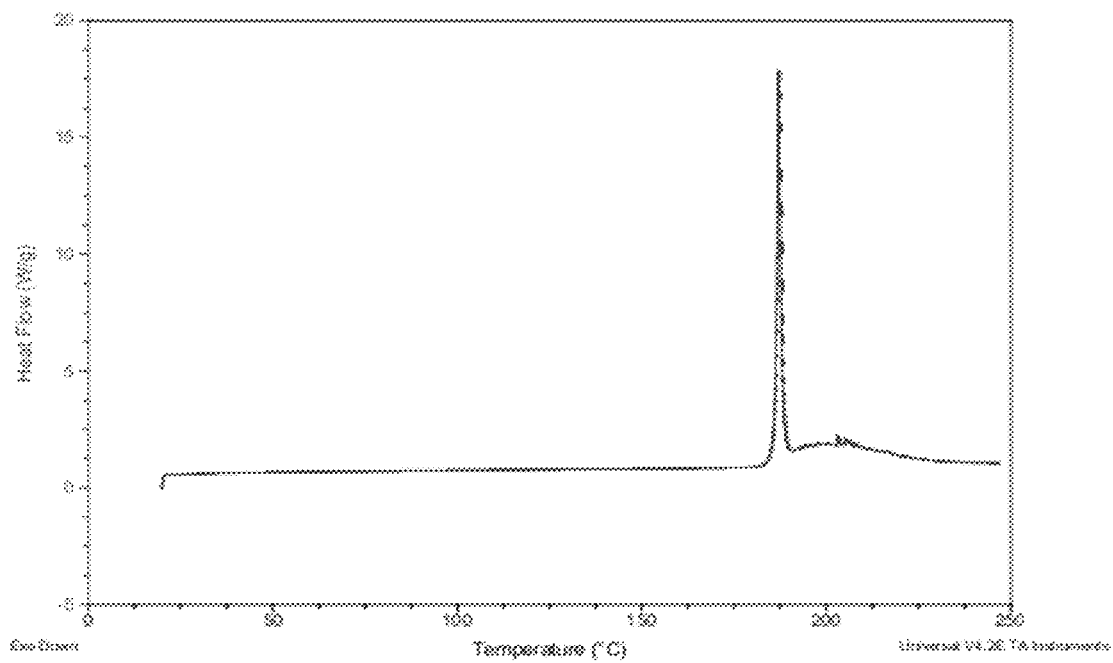
Figure 4. DSC thermogram of flupirtine mesilate

Figure 5. IR spectrum of flupirtin mesilate
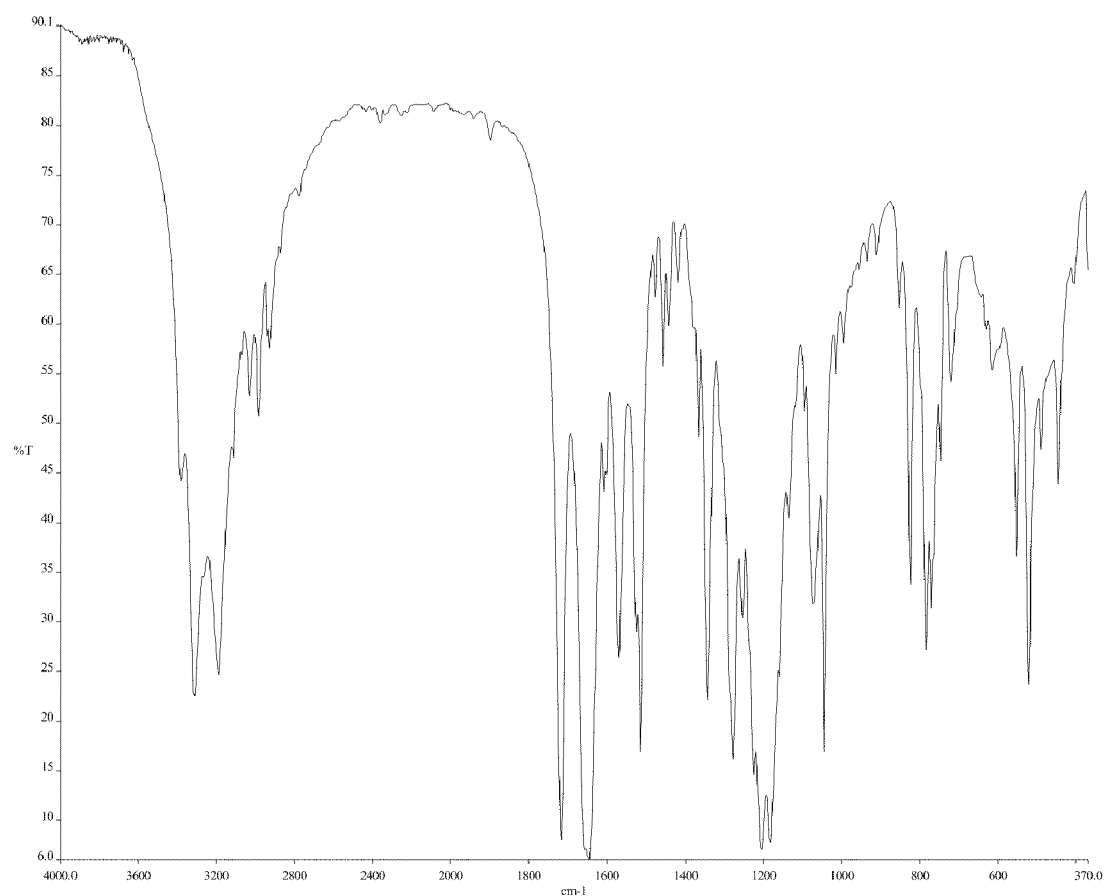

Figure 6. X-ray powder diffraction pattern of flupiritine besilate
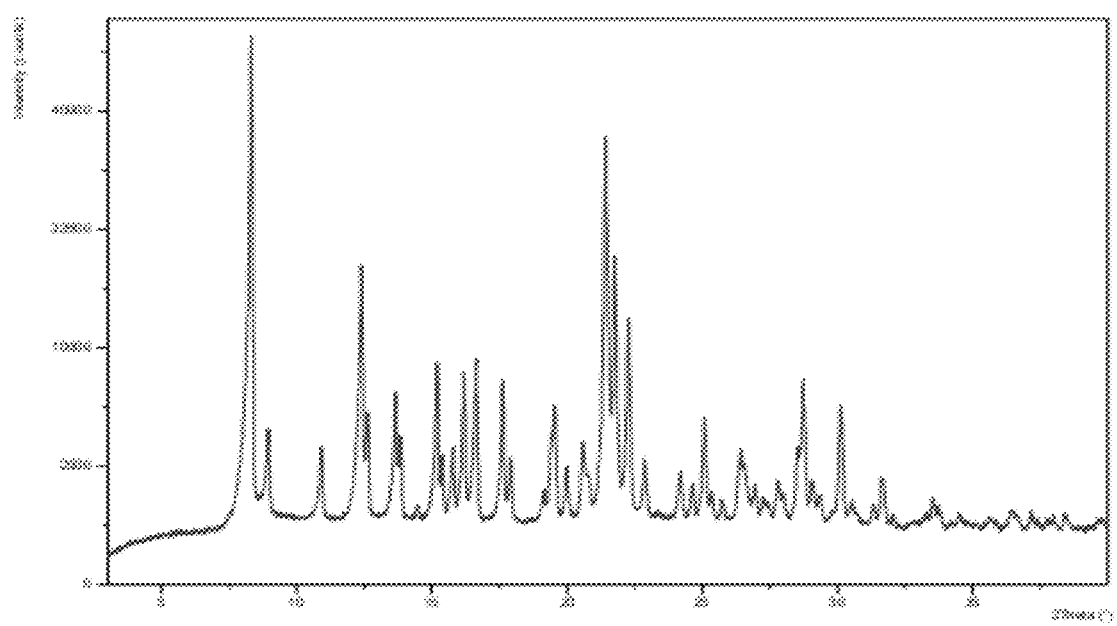

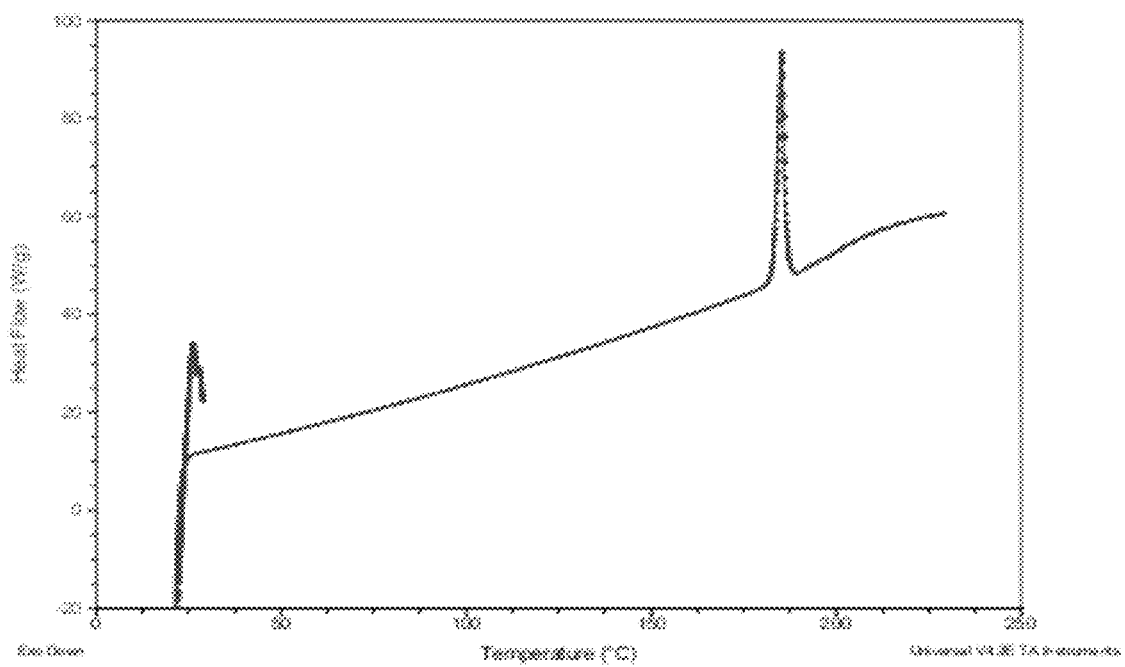
Figure 7. DSC thermogram of flupirtine besilate

SULFONATE SALTS OF 2-AMINO-3-CARBETHOXYAMINO-6-(4-FLUORO-BENZYLAMINO)-PYRIDINE

CROSS-REFERENCE TO RELATED APPLICATIONS

This application claims the benefit of European patent application no. 08010471.4, filed Jun. 9, 2008, which is incorporated herein by reference in its entirety.

TECHNICAL FIELD

The present invention relates to sulfonic acid addition salts of flupirtine, to processes for producing said salts and pharmaceutical compositions comprising thereof, and to therapeutic uses thereof.

BACKGROUND 2-amino-3-carbethoxyamino-6-(4-fluoro-benzylamino)-pyridine ("Flupirtine") of the following formula (1):

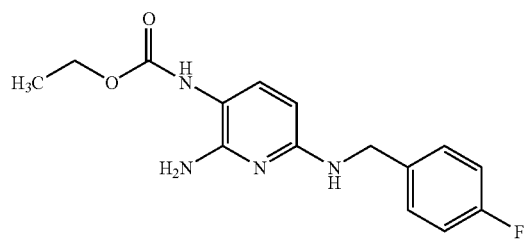

is a centrally active non-opioid analgesic which does not cause any addiction or tolerance development. It is also a muscle-relaxant.

Flupirtine has a unique spectrum of pharmacological activity. It is used in the treatment and prevention of acute and chronic pain including neuropathic pain, nerve pain, cancer pain, vasomotor and migraine headaches, post-operative pain, post-traumatic pain, burn pain, erosion pain, dental pain and the pain associated with degenerative and inflammatory joint disease.

Flupirtine is also used in the treatment and prevention of muscular tension, muscle spasm and muscle stiffness. It is particularly useful in the treatment of back pain. Additionally, flupirtine also exerts potent cyto- and neuroprotective effects and has utility in the treatment and prevention of neurodegenerative disorders such as Parkinson's disease, dementia including Alzheimer's disease, Huntington's chorea, multiple sclerosis, amyotrophic lateral sclerosis, encephalopathy including AIDS related encephalopathy, Creutzfeldt-Jakob disease including classical and new-variant types and Batten disease. Flupirtine also has utility in the treatment and prevention of diseases of the eye such as maculopathy including senile macular degeneration, diabetic retinopathy, glaucoma and retinitis pigmentosa. Flupirtine also has utility in the treatment and prevention of myocardial ischemia and infarction, cerebral ischemia and infarction, shock, tinnitus and hepatitis.

Flupirtine is commonly used in the form of pharmaceutically acceptable acid addition salts. Commercially, flupirtine is available as its maleate addition salt under the trademark Katadolon®.

There are two known polymorphs of flupirtine maleate, designated in the art as flupirtine maleate A and B. European patent EP 0 977 736 discloses pure flupirtine maleate crystalline form A and a process for its preparation. Flupirtine and mixtures of flupirtine maleate polymorphs A and B and pure polymorph B can be synthesised according to DE 3133519.

Other known flupirtine salts are flupirtine chloride, reported in German patent DE 1 795 858, and flupirtine gluconate, reported in European patent EP 0 160 865. WO 2004/112754 discloses several acid addition salts of flupirtine and their use in lyophilisates for parenteral solutions. For example, the flupirtine gluconate acid addition salt was prepared by lyophilisation and obtained in amorphous form.

Polymorphs A and B of flupirtine maleate are both characterized by an acicular morphology. The extremely fine needle structure of flupirtine maleate poses difficulties in the formulation process as is, for example, reported in EP 1 795 186. In particular, the acicular structure poses difficulties in the development of controlled release formulations of flupirtine as is described in patents EP 0 615 754 and EP 1 795 186. Furthermore, due to the acicular morphology, polymorphs A and B of flupirtine maleate have a very low bulk density and poor flowability causing difficulties in the formulation process. As a consequence, dosing of flupirtine maleate is difficult and the reproducibility of the formulation process is poor. These characteristics of flupirtine maleate necessitate a costly additional mechanical treatment of the drug substance for proper further processing.

In addition, flupirtine maleate is sensitive to oxygen and poorly soluble in water. It is also known to form an isopropanol solvate, as reported in "Polymorphism and desolvation of flupirtine maleate", *European Journal of Pharmaceutics and Biopharmaceutics* 46 (1998) 329-337.

It is the object of the present invention to provide acid addition salts of flupirtine which are characterized by an improved balanced mix of solubility, oxidation stability and morphology, i.e., possessing a less acicular morphology. Furthermore, it is also the object of the present invention to provide pharmaceutical compositions comprising said flupirtine-addition salts as active ingredient, to processes for producing said salts and pharmaceutical compositions, and to therapeutic uses thereof.

SUMMARY

In one embodiment, the present invention relates to flupirtine sulfonic acid addition salts having the following formula (2),

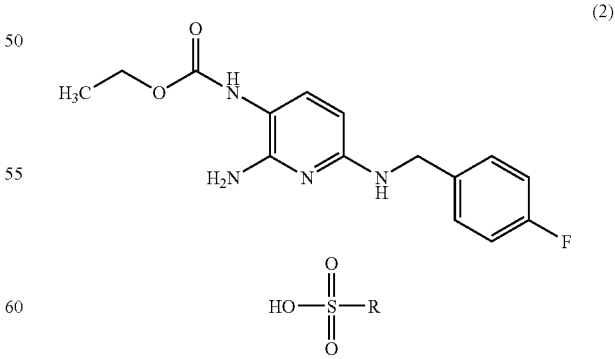

wherein R represents a substituted or unsubstituted $C_1$-$C_{12}$-alkyl or $C_6$-$C_{10}$-aryl group.

In another embodiment, the acid addition salts having formula (2) may be prepared by a process comprising reacting flupirtine base (2-amino-3-carbethoxyamino-6-p-fluorobenzylamino-pyridine) and an acid having the following formula

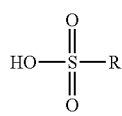

providing a reaction mixture from which the said acid addition salt precipitates, wherein R represents a substituted or unsubstituted $C_1$-$C_{12}$-alkyl or $C_6$-$C_{10}$-aryl group.

In one embodiment, the present invention provides pharmaceutical compositions comprising at least one of the above flupirtine acid addition salts and their crystalline forms and at least one pharmaceutically acceptable excipient.

In another embodiment, the present invention also encompasses a pharmaceutical composition comprising at least one of the above described flupirtine acid addition salts and their crystalline forms prepared according to the processes of the present invention, and at least one pharmaceutically acceptable excipient.

In another embodiment, the invention encompasses a process for preparing a pharmaceutical composition comprising combining at least one of the above-described acid addition salts and their crystalline forms, and at least one pharmaceutically acceptable excipient.

In another embodiment, the invention encompasses the use of at least one of the above described flupirtine acid addition salts and their crystalline forms for the manufacture of a medicament for the treatment and prevention of acute and chronic pain, pain associated with degenerative and inflammatory joint disease, muscular tension, muscle spasm, burn pain, muscle stiffness, neurodegenerative disorders, dementia, encephalopathy, diseases of the eye, myocardial ischemia and infarction, cerebral ischemia and infarction, shock, tinnitus and hepatitis.

In another embodiment, the invention encompasses the use of at least one of the above described flupirtine acid addition salts and their crystalline forms for the manufacture of a pharmaceutical composition.

In yet another embodiment, the invention encompasses a method of treating and preventing of acute and chronic pain, pain associated with degenerative and inflammatory joint disease, muscular tension, muscle spasm, muscle stiffness, neurodegenerative disorders, dementia, encephalopathy, diseases of the eye, myocardial ischemia and infarction, cerebral ischemia and infarction, shock, tinnitus and hepatitis, comprising administering a pharmaceutical composition comprising at least one of the above described flupirtine acid addition salts and their crystalline forms to a patient in need thereof.

BRIEF DESCRIPTION OF THE FIGURES

FIG. 1 depicts a photomicrograph of flupirtine mesilate.
FIG. 2 depicts a photomicrograph of flupirtine maleate.
FIG. 3 depicts an X-ray powder diffraction pattern of flupiritine mesilate.
FIG. 4 depicts a DSC thermogram of flupirtine mesilate.
FIG. 5 depicts an IR spectrum of flupirtine mesilate.
FIG. 6 depicts an X-ray powder diffraction pattern of flupiritine besilate.

FIG. 7 depicts a DSC thermogram of flupirtine besilate.
FIG. 8 depicts an IR spectrum of flupirtine besilate.

DETAILED DESCRIPTION

As referred to herein, the "aspect ratio" denotes the ratio of the second largest dimension of a crystal particle (i.e. its width) to the largest dimension of the crystal particle (i.e. its length). The aspect ratio may be determined from a representative number of crystals by visual observation under a light microscope.

As referred to herein, the term "substantially less acicular" denotes crystalline particles having an aspect ratio of 0.1 or greater. Preferably, the aspect ratio is between 0.2 and 1.0, preferably between 0.3 and 0.9, more preferably between 0.4 and 0.8, and most preferably between 0.6 and 0.7.

As referred to herein, the term "crystalline particles" preferably denotes crystalline flupirtine acid addition salts characterised as having a mean particle size of greater than 30 μm. Preferably, the mean particle size is greater than 50 μm, more preferably greater than 100 μm, even more preferably greater than 150 μm, and most preferably greater than 200 μm. Furthermore, for reasons of formulation efficiency, it is preferred that the mean particle size is less than 1000 μm, preferably less than 500 μm, even more preferably less than 300 μm, and most preferably less than 250 μm.

As defined herein, the term "particle size" refers to the size of the largest dimension of a crystal particle, and the mean particle size is determined from a representative number of crystals. The particle size may be determined by visual observation under a light microscope. As referred to herein, the term "storage form" denotes a flupirtine salt to which the free flupirtine base is converted by acidification for the purpose of later conversion of said salt to another flupirtine salt. For example, according to the above definition, flupirtine mesilate would be a storage form of flupirtine if flupirtine mesilate is produced and subsequently converted to e.g. flupirtine gluconate or flupirtine maleate.

While the flupirtine chloride salt is sensitive to oxidation and has poor storage stability, the flupirtine gluconate salt is also not stable against oxidation (but due to its high solubility is suitable for an injectable formulation), and flupirtine maleate salts are sensitive to oxygen and poorly soluble in water, the salts of the present invention are characterized by storage stability, a markedly less acicular morphology than the prior know flupirtine salts, stability toward oxidation, reduced discolouration as pure compounds or when used with common pharmaceutical excipients and an improved solubility in water and alcohols.

The present invention relates to acid addition salts having the following formula (2),

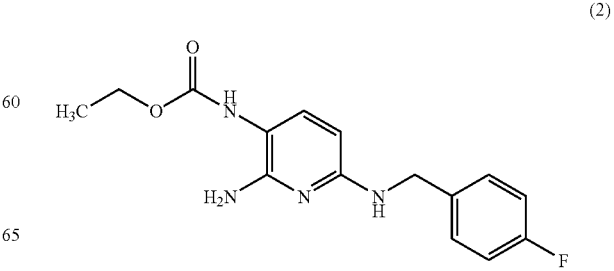

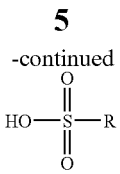

wherein R represents a substituted or un-substituted $C_1$-$C_{12}$-alkyl or $C_6$-$C_{10}$-aryl group.

Suitable $C_1$-$C_{12}$-alkyl groups comprise methyl, ethyl, n-propyl, isopropyl, n-butyl, sec-butyl, tert-butyl, pentyl, hexyl, cyclohexyl, heptyl, octyl, nonyl, decyl and dodecyl.

Suitable $C_6$-$C_{10}$-aryl groups comprise phenyl and naphthyl.

The $C_1$-$C_{12}$-alkyl or $C_6$-$C_{10}$-aryl groups may be substituted. Suitable substituents include and are not limited to hydroxyl, $C_1$-$C_4$-alkoxy, phenoxy, halogen, COOH, $C_1$-$C_4$-alkyl, and phenyl.

Preferred substituents include hydroxyl, methoxy, ethoxy, phenoxy, fluoro, chloro, bromo, iodo, methyl, ethyl, n-propyl, isopropyl, n-butyl, sec-butyl, tert-butyl and phenyl as well as further sulfonic acid groups.

Preferred examples of acid components in above formula (2) comprise methane sulfonic acid, ethane sulfonic acid, n-propane sulfonic acid, n-butane sulfonic acid, dodecane sulfonic acid, phenylethane sulfonic acid, hydroxyethane sulfonic acid, methoxyethane sulfonic acid, benzene sulfonic acid, halogenbenzene sulfonic acid, methoxybenzene sulfonic acid, toluene sulfonic acid, 5-salicylsulfonic acid, naphthalene sulfonic acid, and naphthalene disulfonic acid.

Preferred examples of halogenbenzene sulfonic acid comprise 4-fluorobenzene sulfonic acid 4-chlorobenzene sulfonic acid and 4-bromobenzene sulfonic acid.

Preferred examples of naphthaline sulfonic acid include 1-naphthaline sulfonic acid and 2-naphthaline sulfonic acid.

Preferably, the acid component in the above formula (2) is methane sulfonic acid or benzene sulfonic acid.

In the above acid addition salt of formula (2), the mole ratio of the acid component to the flupirtine base component is 1:1 to 1:1.3, preferably 1:1.2, more preferably 1:1 to 1:1.1, and most preferably 1:1, respectively.

Furthermore, the present invention also relates to a population of crystalline flupirtine acid addition salts of formula (2) characterised in that at least 50 mol-%, preferably at least 60 mol-%, more preferably at least 70 mol-%, even more preferably at least 80 mol-% and most preferably at least 90 mol-% of the crystalline particles have a non-acicular morphology.

For example, flupirtine mesilate crystallizes in the form of short columns. The substantially less acicular morphology of the salts of the invention can be exemplified by comparison of flupirtine mesilate to flupirtine maleate: FIG. 1 depicts a photomicrograph of flupirtine mesilate whereas FIG. 2 depicts a photomicrograph of flupirtine maleate.

Furthermore, the markedly less acicular morphology of the crystals allows better flowability and dosing. Thus, the improved crystal shape of the flupirtine salts according to formula (2) overcomes the processing difficulties inherent to acicular flupirtine salts such as flupirtine maleate.

The less acicular morphology of flupirtine salts of the salts of formula (2) also results in a much higher bulk density (see example 5), which is advantageous for formulations.

In contrast to other acid addition salts, for example, maleate and gluconate or inorganic salts, the sulfonate acid addition salts of flupirtine of the present invention, especially mesilate and the besilate, show substantially improved stability towards oxidation (see example 5) and towards discolouration, when exposed to air for a storage period of 30 days at room temperature. Discolouration can occur after prolonged storage or when exposed to air. This effect can be simulated using stress conditions: Elevated temperature and/or moisture. Discolouration is regarded as leading to an active pharmaceutical ingredient (API) of low pharmaceutical quality and can be avoided by using a protective atmosphere in the production process and using expensive packaging materials for the finished drug forms. The discolouration effect is known for flupirtine hydrochloride, flupirtine gluconate and both polymorphs of flupirtine maleate.

Furthermore, under dry conditions, in the absence of oxygen, the sulfonic acid addition salts of the present invention are also characterized by improved thermal stability as is evident from stress tests under nitrogen at elevated temperatures (e.g. 70° C.).

Consequently, the compounds according to formula (2) are characterized by markedly superior storage stability than prior known flupirtine salts.

In addition, the compounds of formula (2) do not form solvates with a variety of solvents such as alcohols, water or methylene chloride. This is a significant advantage, because it is difficult to remove solvents from an API when preparing a formulation. The level of difficulty depends on the particle morphology and the temperature at which desolvatation occurs. For the flupirtine maleate salts, the temperature of desolvatation is from about 80° C. to about 100° C., which is relatively high. The amount of impurities in the salt could increase if heated. The absence of solvates can be determined by DSC analysis (see FIGS. 4 and 7).

These properties make the flupirtine salts of formula (2) ideally suited as storage form.

In another aspect of the invention, the salts of flupirtine with organosulfonic acids having 6 or less than 6 carbon atoms show better solubility in aqueous media compared to the currently available maleate form by factor 2 to 3.25 (see example 7 herein).

The acid addition salts having the following formula (2) may be prepared by a process comprising reacting flupirtine base (2-amino-3-carbethoxyamino-6-p-fluorobenzylamino-pyridine) an acid having the following formula

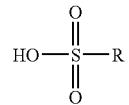

providing a reaction mixture from which the said acid addition salt precipitates, wherein R represents a substituted or unsubstituted $C_1$-$C_{12}$-alkyl or $C_6$-$C_{10}$-aryl group.

The free flupirtine base can be prepared by known processes as are described, for example, in European patent no. EP 0 977 736, example 2.

In some embodiments, the addition salts are prepared by reacting flupirtine and an acid in a solvent providing a reaction mixture from which the said acid addition salt precipitates. In preferred embodiments, a solution of flupirtine in the solvent is reacted with the acid.

Preferably, the reaction mixture is heated to aid the salt formation, if required. Preferably, heating is to a temperature of about 30° C. to about 60° C., more preferably, to about 40° to 50° C. Preferably, to avoid oxidation, a protective atmosphere like nitrogen or argon may be used in this reaction.

Examples for suitable solvents include but not limited to ethers, alcohols, ketones, esters, halogenated solvents, nitriles, water, or mixtures thereof.

Preferably, the ethers are $C_3$-$C_7$ ethers, the alcohols are $C_1$-$C_5$ alcohols, the ketones are $C_3$-$C_5$ ketones, the esters are $C_2$-$C_6$ esters, the halogenated solvents are $C_1$-$C_6$ halogenated solvents and the nitriles are $C_2$-$C_3$ nitriles. More preferably, the $C_1$-$C_6$ halogenated solvents are $C_1$-$C_6$ chlorinated solvents and the $C_2$-$C_6$ esters are $C_2$-$C_6$ acetates.

Preferably, the $C_3$-$C_7$ ethers are diethyl ether, diisopropyl ether, or t-butyl methyl ether, or mixtures thereof. Preferably, the $C_1$-$C_5$ alcohols are methanol, ethanol, isopropanol, n-propanol, n-, iso-, or tert-butanol, or mixtures thereof. Preferably, the $C_3$-$C_5$ ketones are acetone, methyl ethyl ketone, diethyl ketone or mixtures thereof. Preferably, the $C_2$-$C_6$ esters are methyl-, ethyl-, n-propyl-, i-propyl-, butyl-acetate, or mixtures thereof. Preferably, the $C_1$-$C_6$ halogenated solvents are dichloromethane (DCM), chloroform, cholorobenzene or mixtures thereof. Preferably, the $C_2$-$C_3$ nitriles are acetonitrile, priopionitrile or mixtures thereof. Most preferably, the $C_1$-$C_5$ alcohols are ethanol or iso-propanol. Most preferably, the solvent is a $C_1$-$C_5$ alcohol, more preferably ethanol or iso-propanol.

It is further preferred that the solution of flupirtine is reacted with about 1 to about 1.3 mole equivalents, preferably about 1 to about 1.2 mole equivalents, most preferably about 1 to about 1.1 mole equivalents, of the corresponding sulfonic acid per mole equivalent of flupirtine base. Preferably, the sulfonic acid is methane sulfonic acid or benzene sulfonic acid.

Preferably, the said reaction mixture is preferably a solution from which the acid addition salt precipitates.

Precipitation occurs either on its own motion or is induced by reducing the solvent volume and/or the temperature and/or by adding an anti-solvent and/or by adding seeding crystals.

Typically, the anti-solvent is such that is less polar than the reaction solvent and thus when added to the solution leads to the formation of a precipitate of the said salt. Examples for such solvent can be anyone of the above solvents as well as toluene, benzene, hexane, cyclohexane and pentane.

Preferably, the temperature is reduced to about 0° C. to about 10° C., more preferably to about 5° C.

The precipitated salt is collected by filtration and drying, optionally followed by further purification steps. Preferably, drying is performed under reduced pressure for about 12 hours.

According to this procedure flupirtine salts of formula 2 of high purity are obtainable. Preferably, the purity is of more than about 95 Area percent as measured by HPLC. The structure and composition of the obtained salts prepared can be confirmed by the usual analytical methods such as NMR spectrometry, IR spectrometry, elemental analysis, DSC analysis, and the determination of the melting point (see examples 1 and 2 and FIGS. 3-8).

The salts prepared by the method described above can be further purified by recrystallization from appropriate solvents, if necessary. Examples of such solvents include isopropanol, acetone, methylene chloride and chloroform.

Furthermore, the salts of the invention can further be purified by conversion to the flupirtine free base, followed by extraction or crystallization and renewed acidification.

In the above process for preparing the acid addition salt of formula 2, the acid is selected from methane sulfonic acid, ethane sulfonic acid, n-propane sulfonic acid, n-butane sulfonic acid, dodecane sulfonic acid, phenylethane sulfonic acid, hydroxyethane sulfonic acid, methoxyethane sulfonic acid, benzene sulfonic acid, halogenbenzene sulfonic acid, methoxybenzene sulfonic acid, toluene sulfonic acid, 5-salicylsulfonic acid, naphthalene sulfonic acid, and naphthalene disulfonic acid.

Preferred examples of halogenbenzene sulfonic acid comprise 4-fluorobenzene sulfonic acid 4-chlorobenzene sulfonic acid and 4-bromobenzene sulfonic acid.

Preferred examples of naphthaline sulfonic acid include 1-naphthaline sulfonic acid and 2-naphthaline sulfonic acid.

Preferably, the acid component is methane sulfonic acid or benzene sulfonic acid.

When the acid is methane sulfonic acid and the solvent is, preferably, selected from the list consisting of ethers, alcohols, ketones, esters, halogenated solvents, water or mixtures thereof, a crystalline form of flupirtine mesilate is obtained. The preferred list of solvents is mentioned before.

In one embodiment, the present invention provides a crystalline form of flupirtine mesilate characterized by data selected from the group consisting of: a powder XRD pattern with peaks at about 5.3, 10.6, 15.8, 19.5 and 22.1±0.2 degrees two theta, a powder XRD pattern as depicted in FIG. 3; and a combination thereof.

The above crystalline form of flupirtine mesilate can be further characterized by data selected from the group consisting of: a photomicrograph as depicted in FIG. 1, a powder XRD pattern with peaks at about 13.0, 14.0, 17.3, 20.4 and 26.5±0.2 degrees 2-theta, a DSC peak at about 187±2° C., a DSC pattern as depicted in FIG. 4, a FT-IR spectrum with peaks at about 3383, 3315, 3189, 1718, 1647, 1570 and 1516 $cm^{-1}$±2 $cm^{-1}$, and an IR pattern as depicted in FIG. 5; and a combination thereof.

Also, when the acid is benzene sulfonic acid and the solvent is, preferably, selected from the list consisting of ethers, alcohols, ketones, esters, halogenated solvents, water or mixtures thereof a crystalline form of flupirtine besilate is obtained. The preferred list of solvents is mentioned before.

In one embodiment, the present invention provides a crystalline form of flupirtine besilate, characterized by data selected from the group consisting of: a powder XRD pattern with peaks at about 8.3, 12.4, 15.2, 21.4 and 28.7±0.2 degrees two theta, a powder XRD pattern as depicted in FIG. 6; and a combination thereof.

The above crystalline form of flupirtine besilate can be further characterized by data selected from the group consisting of: a powder XRD pattern with peaks at about 9.0, 10.9, 13.7, 16.2, 16.6, 17.6, 21.8, 22.3±0.2 degrees two-theta, a DSC peak at about 185±2° C., a DSC pattern as depicted in FIG. 7, a FT-IR spectrum with peaks at about 3459, 3346, 1718, 1654, 1558 and 1513±2 $cm^{-1}$, and an IR pattern as depicted in FIG. 8; and a combination thereof.

The salts of the invention and also their crystalline forms are particularly well suited for solid pharmaceutical formulations. The crystals of the salts of the present invention are more easily coated and, thus, the formulation difficulties inherent to prior compositions utilizing acicular flupirtine salts are overcome.

In one embodiment, the present invention provides pharmaceutical compositions comprising at least one of the above flupirtine acid addition salts and their crystalline forms and at least one pharmaceutically acceptable excipient. Optionally, prior known flupirtine salts such as flupirtine maleate and gluconate can also be used in addition to the compounds of the invention.

The pharmaceutical compositions of the invention may also comprise one or more auxiliary excipients such as for example carriers, diluents, binders, lubricants, surfactants, disintegrants, plasticisers, anti-tack agents, opacifying agents, pigments, anti-oxidants and the like. As will be appreciated by those skilled in the art, the exact choice of excipient and relative amount will depend on the type of pharmaceutical composition, the API, dosage and other factors.

In another embodiment, the present invention also encompasses a pharmaceutical composition comprising at least one of the above described flupirtine acid addition salts and their crystalline forms prepared according to the processes of the present invention, and at least one pharmaceutically acceptable excipient.

In another embodiment, the invention encompasses a process for preparing a pharmaceutical composition comprising combining at least one of the above described flupirtine acid addition salts and their crystalline forms and at least one pharmaceutically acceptable excipient.

In another embodiment, the invention encompasses the use of at least one of the above described flupirtine acid addition salts and their crystalline forms for the manufacture of a medicament for treatment and prevention of acute and chronic pain, pain associated with degenerative and inflammatory joint disease, muscular tension, muscle spasm, muscle stiffness, neurodegenerative disorders, dementia, encephalopathy, diseases of the eye, myocardial ischemia and infarction, cerebral ischemia and infarction, shock, tinnitus and hepatitis.

In another embodiment, the invention encompasses the use of at least one of the above described flupirtine acid addition salts and their crystalline forms for the manufacture of a pharmaceutical composition.

In yet another embodiment, the invention encompasses a method of treating and preventing of acute and chronic pain, pain associated with degenerative and inflammatory joint disease, muscular tension, muscle spasm, muscle stiffness, neurodegenerative disorders, dementia, encephalopathy, diseases of the eye, myocardial ischemia and infarction, cerebral ischemia and infarction, shock, tinnitus and hepatitis, comprising administering a pharmaceutical composition comprising at least one of the above described flupirtine acid addition salts and their crystalline forms to a patient in need thereof.

The present invention is further illustrated by the following examples.

EXAMPLES

HPLC Method

| Column | Reversed phase silica gel column |
| --- | --- |
| Mobile Phase A | MeCN-10%/0.02 M NH4H2PO4 aq |
| Mobile Phase B | MeCN-80%/0.02 M NH4H2PO4 aq |
| Gradient | Time (min) | Mobile Phase A (% vol/vol) | Mobile Phase B (% vol/vol) |
| | 0 | | 0 |
| | 2 | | 0 |
| | 10 | | 15 |
| | 50 | | 100 |
| | 55 | | 100 |
| | 56 | | 0 |
| | 61 | | 0 |
| Flow Rate | 1.0 ml/mm |
| Detector | λ = 248 nm; |
| Column Temperature | Room temperature (25° C.) |
| Injection Volume | 20 μl |

Melting Point

Melting point was measured with the Mettler-Toledo FP apparatus.

X-Ray Powder Diffraction Analysis (XRPD)

XPRD was measured with a Philips X'Pert PRO powder diffractometer with the following parameters.

| Sample holder preparation | Samples after being powdered in a mortar and pestle are applied directly on silicon PW1817/32 "zero background" holder |
| --- | --- |
| Instrument | Philips X'Pert PRO |
| Goniometer | PW3050/60 |
| Generator | PW3040; 45 kV, 40 mA |
| X-Ray tube | PW3373/00; Cu anode LFF |
| X-ray radiation | $\lambda(CuK\alpha_1)$ = 1.540598 Å |
| Temperature | 295 ± 5° K |

Differential Scanning Calorimetry (DSC) Analysis

DSC was measured using a TA Instrument, scanning from 20° C. to 100° C. at a scan rate of 10° C./minute. A sample was placed in a closed aluminum pan and the reference pan was prepared the same.

Example 1

Preparation of 2-amino-3-carbethoxyamino-6-(4-fluoro-benzylamino)-pyridine Mesilate Under nitrogen atmosphere 30 g of 2-amino-3-carbethoxyamino-6-(4-fluoro-benzylamino)-pyridine and 9.7 g of methane sulfonic acid were added to 1000 ml of isopropanol at 20° C. The mixture was heated to 60° C. with stirring for 30 min. A transparent solution was formed. The mixture was cooled down to 5° C. and left overnight for crystallization. Within 12 hours white crystals of flupirtine mesilate were formed. The crystals were removed from the solution by filtration. As a result of drying 28.0 g of flupirtine mesilate were obtained.

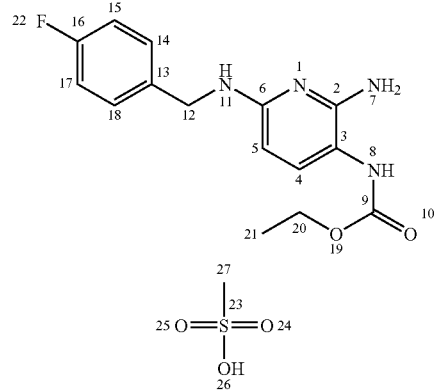

$^1$H-NMR (DMSO-d6, 400 Mhz): δ (ppm)=1.20 (3H, m, 21-CH$_3$), 2.43 (3H, s, 27-CH$_3$), 4.01-4.04 (2H, m, 20-CH$_2$), 4.43 (2H, s, 12-CH$_2$), 5.22 (2H, s, 7-NH$_2$), 5.88 (1H, d, J=12 Hz, 5-CH), 6.53-6.65 (1H, m, 11-NH), 7.16-7.21 (1H, t, 4-CH$_2$), 7.38-7.42 (2H, m, 15/17-CH), 7.48 (2H, d, J=8 Hz, 14/18-CH), 7.91 (1H, s, br, —OH), 8.54 (1H, s, 8-NH).
m.p. 186, 7° C.

Example 2

Preparation of 2-amino-3-carbethoxyamino-6-(4-fluoro-benzylamino)-pyridine Besilate Under nitrogen atmosphere 30 g of 2-amino-3-carbethoxyamino-6-(4-fluoro-benzylamino)-pyridine and 15.8 g of benzene sulfonic acid were added to 1000 ml of isopropanol at 20° C. The mixture was heated to 60° C. during stirring for 30 min. A transparent solution was formed. The mixture was cooled down to 5° C. and left overnight for crystallization. The crystals were removed from the solution through filtration. As a result of drying 34.8 g of flupirtine besilate were obtained.

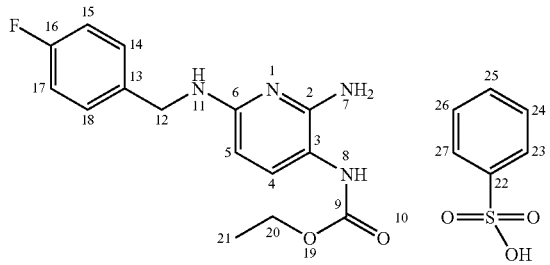

$^1$H-NMR (DMSO-d6, 400 Mhz): δ (ppm)=1.19 (3H, t, br, J=8 Hz, 21-CH$_3$), 4.00-4.05 (2H, m, 20-CH$_2$), 4.35 (2H, d, J=8 Hz, 12-CH$_2$), 5.22 (2H, s, 7-NH$_2$), 5.89 (1H, d, 5-CH), 6.53-6.65 (1H, t, 11-NH), 7.19 (3H, t, J=8 Hz, 15/17-CH), 7.30-7.40 (3H, m, 26/25/24-CH), 7.35-7.42 (2H, m, 14/18-CH), 7.45-7.49 (1H, d, br, J=8 Hz, 4-CH), 7.56-7.63 (2H, m, 23/27-CH), 8.18 (1H, s, 8-NH).

m.p. 181.0° C.

Example 3

Preparation of 2-amino-3-carbethoxyamino-6-(4-fluoro-benzylamino)-pyridine Tosilate 30 g of Flupirtine base were dissolved in 1200 ml of Isopropanol at 50° C. 18 g of p-Toluenesulphonic acid were dissolved in 200 ml of Isopropanol at 20° C. At 40° C. the p-Toluenesulphonic acid solution was added to the solution of flupirtine base. Then the mixture was cooled down to 20° C. The mixture was stirred for 60 min. Then the sediment was filtered. 45.0 g of the product was formed.

Example 4

Preparing Photomicrographs of Flupirtine Sulfonate Salts

The photomicrographs were obtained by gently exerting pressure on the sample material with a mortar and pistil, transferring sample material to a microscope slide and covering it with immersion oil, followed by observation and image recording on an Optech Biostar microscope equipped with a polarisation filter. The magnification was 200, i.e. at a width of the photomicrograph of 14 cm, 1 cm of said photograph corresponds to about 0.06 mm.

Example 5

Preparation of Flupirtine Maleate Forms A and B
Flupirtine Base was Prepared According to patent EP 0 977 736

Flupirtine Maleate Form A 30 g of Flupirtine base were dissolved in 1080 ml of isopropanol at 50° C. 12.8 g of Maleic acid was dissolved in 96 ml of isopropanol at 20° C. Flupirtine solution was cooled down to 20° C. Maleic acid solution was added to Flupirtine solution in the course of stirring. The sediment was formed almost at once. The mixture was heated and stirred for 60 min at 60° C. Then the mixture was cooled down to 20° C. The sediment was filtered and washed three times with cooled (0° C.) Isopropanol. The sediment formed was white. 41.4 g of the product was formed.

Flupirtine Maleate B 30 g of Flupirtine base were dissolved in 1080 ml of Isopropanol at 60° C. 12.8 g of Maleic acid was dissolved in 96 ml of Isopropanol. 0.2 g of flupirtine maleate B crystals made according EP 977 736 patent were added. Flupertine Maleate B was made according EP 977 736 through heating of part of Maleat A for 2 h at 150° C. Maleic acid solution was added to Flupirtine solution at 60° C. in the course of stirring. The mixture was stirred for 2 minutes and cooled down to 17° C. The sediment formed was filtered. The colour of the sediment was white. 40.9 g of the product was formed.

Example 5

Oxidative Stability of Flupirtine Sulfonic Acid Salts

HPLC analysis was performed after isolation and drying of flupirtine maleate form A and flupirtine sulfonate salts and repeated after 14 days of storage at room temperature under open air.

| Salt form | Flupirtine signal after 0 days (area under the peak in, %) | Flupirtine signal after 14 days (area under the peak in, %) |
|---|---|---|
| Flupirtine maleate A | 99.27 | 96.18 |
| Flupirtine besilate | 96.93 | 96.87 |
| Flupirtine mesilate | 97.69 | 96.81 |

As is evident from the table, the area under the peak of the flupirtine signal decreased by 3.11% for flupirtine maleate form A as compared to less than 0.1% for flupirtine besilate.

Example 6

Bulk Density of Flupirtine Sulfonate Salts

| Salt form | Bulk density (ml/100 g substance) |
|---|---|
| Maleate Form A | 686 |
| Maleate Form B | 1634 |
| Flupirtine besilate | 358 |
| Flupirtine mesilate | 478 |
| Flupirtine tosilate | 420 |

The bulk density was determined as follows: Without increasing its density, sample material (about 4 grams) was introduced into a 10 ml measuring cylinder (±0.2 ml). The volume and the exact weight of the introduced sample material were determined. The bulk density was calculated as volume per 100.0 g of sample material.

Example 7

Solubility of Flupirtine Sulfonate Salts

The solubility was determined by placing 500 mg of sample material in a 250 ml glass beaker, adding 100 ml of demineralised water and agitating the suspension for 2 hours on a shaker (300 rpm). Subsequently, an aliquot of the solution was centrifuged at 10,000 rpm and the flupirtine absorption was photometrically determined in the supernatant. The amount of flupirtine in solution was calculated with a response factor (absorption/mg substance).

| Salt form | Solubility (mg/100 ml water, 60 min stirring at 20° C.) |
|---|---|
| Maleate Form A | 1.6 |
| Besilate | 3.2 |
| Mesilate | 5.2 |

Example 9

Discolouration Measurements

Method:

Discolouration was measured using optical comparison with a standard: the RAL scale of colours (see list). The colour changes during the experiment were compared to this standard list and the appropriate value was noted. The intensity was increasing on a scale ranging from 1 to 10.

A higher number means more discolouration. The increase in colour intensity is not proportional but qualitative.

The colouration of flupirtine maleate and flupirtine mesilate has been observed at 60° C. and at 70° C. with the substance alone and in mixture with micro crystalline cellulose (MCC), with lactose or with dicalcium phosphate DiCaPhos (CaHPO$_4$). The tests were performed under dry and neat conditions. Neat refers to saturated with moisture, i.e., 100% relative humidity (rh). All experiments showed equal or less discolouration with mesilate compared to maleate. Only with lactose moisture had to be avoided for the mesilate.

At temperatures above 65° C. saturated moisture should be generally avoided when using flupirtine salts.

TABLE 1

Ranking of observed colouration RAL standard colours as defined by the RAL institute St. Augustin Germany (www.ral.de).

| relative intensity of colouration | colour hue | RAL number |
|---|---|---|
| 1 | Signal white | 9003 |
| 2 | Cream | 9001 |
| 3 | Light ivory | 1015 |
| 4 | Ivory | 1014 |
| 5 | Beige | 1001 |
| 6 | Curry | 1027 |
| 7 | Ochre brown | 8001 |
| 8 | Clay brown | 8003 |
| 9 | Olive brown | 8008 |
| 10 | Chocolate brown | 8017 |

TABLE 2

Colouration of flupirtine maleate vs. flupirtine mesilate

| Days | 0 | 2 | 4 | 7.5 | 13 |
|---|---|---|---|---|---|
| flupirtine maleate 60° C. dry | 2 | 2 | 3 | 3 | 3 |
| flupirtine maleate 60° C. 100% rh | 2 | 2 | 3 | 3 | 4 |
| flupirtine maleate 70° C. dry | 2 | 2 | 3 | 3 | 3 |
| flupirtine maleate 70° C. 100% rh | 2 | 2 | 3 | 3 | 3 |
| flupirtine mesilate 60° C. dry | 1 | 1 | 1 | 1 | 2 |
| flupirtine mesilate 60° C. 100% rh | 1 | 1 | 2 | 2 | 3 |
| flupirtine mesilate 70° C. dry | 1 | 1 | 2 | 2 | 3 |
| flupirtine mesilate 70° C. 100% rh | 1 | 1 | 2 | 3 | 4 |
| Binary mixture with MCC | | | | | |
| flupirtine maleate + MCC 60° C. dry | 2 | 2 | 3 | 3 | 3 |
| flupirtine maleate + MCC 60° C. 100% rh | 2 | 2 | 3 | 4 | 4 |
| flupirtine maleate + MCC 70° C. dry | 2 | 2 | 3 | 3 | 3 |
| flupirtine maleate + MCC 70° C. 100% rh | 2 | 2 | 3 | 4 | 4 |
| flupirtine mesilate + MCC 60° C. dry | 1 | 1 | 1 | 1 | 2 |
| flupirtine mesilate + MCC 60° C. 100% rh | 1 | 1 | 2 | 2 | 3 |
| flupirtine mesilate + MCC 70° C. dry | 1 | 1 | 1 | 1 | 2 |
| flupirtine mesilate + MCC 70° C. 100% rh | 1 | 1 | 2 | 2 | 3 |
| Binary mixture with lactose | | | | | |
| flupirtine maleate + lactose 60° C. dry | 2 | 2 | 2 | 2 | 3 |
| flupirtine maleate + lactose 60° C. 100% rh | 2 | 3 | 3 | 4 | 5 |
| flupirtine maleate + lactose 70° C. dry | 2 | 2 | 2 | 3 | 3 |
| flupirtine maleate + lactose 70° C. 100% rh | 2 | 2 | 3 | 4 | 5 |
| flupirtine mesilate + lactose 60° C. dry | 1 | 1 | 1 | 1 | 1 |
| flupirtine mesilate + lactose 60° C. 100% rh | 1 | 2 | 3 | 5 | 8 |
| flupirtine mesilate + lactose 70° C. dry | 1 | 1 | 1 | 1 | 2 |
| flupirtine mesilate + lactose 70° C. 100% rh | 1 | 2 | 2 | 2 | 5 |
| Binary mixture with DiCaPhos | | | | | |
| flupirtine maleate + DiCaPhos 60° C. dry | 2 | 2 | 2 | 2 | 3 |
| flupirtine maleate + DiCaPhos 60° C. 100% rh | 2 | 3 | 3 | 3 | 4 |
| flupirtine maleate + DiCaPhos 70° C. dry | 2 | 2 | 2 | 2 | 3 |
| flupirtine maleate + DiCaPhos 70° C. 100% rh | 2 | 3 | 3 | 3 | 4 |
| flupirtine mesilate + DiCaPhos 60° C. dry | 1 | 1 | 1 | 1 | 1 |
| flupirtine mesilate + DiCaPhos 60° C. 100% rh | 1 | 2 | 2 | 3 | 3 |
| flupirtine mesilate + DiCaPhos 70° C. dry | 1 | 1 | 1 | 1 | 2 |
| flupirtine mesilate + DiCaPhos 70° C. 100% rh | 1 | 2 | 2 | 2 | 3. |

What is claimed is:

1. A crystalline form of flupirtine mesylate characterized by data selected from the group consisting of: a powder XRD pattern with peaks at about 5.3, 10.6, 15.8, 19.5 and 22.1±0.2 degrees two theta, a powder XRD pattern as depicted in FIG. 3; and a combination thereof.

2. A crystalline form of flupirtine besylate characterized by data selected from the group consisting of: a powder XRD pattern with peaks at about 8.3, 12.4, 15.2, 21.4 and 28.7±0.2 degrees two theta, a powder XRD pattern as depicted in FIG. 6; and a combination thereof.

3. A pharmaceutical composition comprising the crystalline form of flupirtine mesylate according to claim 1, and at least one pharmaceutically acceptable excipient.

4. A pharmaceutical composition comprising the crystalline form of flupirtine besylate according to claim 2, and at least one pharmaceutically acceptable excipient.

5. A method of treating or preventing of acute or chronic pain, pain associated with degenerative or inflammatory joint disease, muscular tension, muscle spasm, muscle stiffness, neurodegenerative disorders, back pain, dementia, encephalopathy, diseases of the eye, myocardial ischemia or infarction, cerebral ischemia or infarction, shock, tinnitus and hepatitis, comprising administering a pharmaceutical composition according to claim 3 or claim 4, to a patient in need thereof.

* * * * *